US012758149B2

(12) United States Patent
von Blumenthal et al.

(10) Patent No.: US 12,758,149 B2
(45) Date of Patent: Oct. 13, 2026

(54) PROCESS AND SYSTEM FOR FLUID BALANCING FOR A PATIENT

(71) Applicant: Drägerwerk AG & Co. KGaA, Lübeck (DE)

(72) Inventors: Tilman von Blumenthal, Lübeck (DE); Frank Franz, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 124 days.

(21) Appl. No.: 18/825,107

(22) Filed: Sep. 5, 2024

(65) Prior Publication Data

US 2025/0072829 A1 Mar. 6, 2025

(30) Foreign Application Priority Data

Sep. 6, 2023 (DE) ..................... 10 2023 124 033.1

(51) Int. Cl.

| | |
|---|---|
| ***A61B 5/00*** | (2006.01) |
| ***A61B 5/11*** | (2006.01) |
| ***A61G 7/05*** | (2006.01) |

(52) U.S. Cl.

CPC .......... *A61B 5/4875* (2013.01); *A61B 5/1115* (2013.01); *A61B 5/7271* (2013.01); *A61G 7/0527* (2016.11); *A61B 2560/0443* (2013.01)

(58) Field of Classification Search

CPC ......... A61B 5/00; A61B 5/4875; A61B 5/208; A61B 5/4878; A61B 5/03; G16H 15/00; G16H 50/30; A61G 7/05; A61G 19/44; A61M 5/1723

USPC .................................................. 600/300–301

See application file for complete search history.

(56) References Cited

U.S. PATENT DOCUMENTS

| | | | | |
|---|---|---|---|---|
| 10,456,084 | B1 * | 10/2019 | Lin ..................... | A61G 7/0503 |
| 2008/0198012 | A1 | 8/2008 | Kamen | |
| 2019/0340441 | A1 | 11/2019 | Franz et al. | |
| 2023/0094927 | A1 | 3/2023 | Kawashima et al. | |

FOREIGN PATENT DOCUMENTS

| | | | |
|---|---|---|---|
| DE | 102013017264 | A1 | 4/2015 |
| EP | 3900611 | A1 | 10/2021 |

* cited by examiner

*Primary Examiner* — Boniface N Nganga

(74) *Attorney, Agent, or Firm* — McGlew and Tuttle, P.C.

(57) ABSTRACT

A process and a system for fluid balancing a patient that is in a bed during a predefined reference time period. Each object used is provided with a marking. A bed scale weighs the bed. A reading unit reads the markings on the objects. A camera unit generates images that show at least the bed and objects in the vicinity of the bed. A signal processing unit determines a weight difference between the bed weight of the bed at a first time point and at a second time point. The signal processing unit calculates a fluid balance—the total amount of fluid supplied less the amount of fluid that leaves the patient, during the reference time period. The signal processing unit uses the difference in weight of objects, moved to or from the bed, and the respective amount of fluid that each moved object can hold.

20 Claims, 3 Drawing Sheets

PROCESS AND SYSTEM FOR FLUID BALANCING FOR A PATIENT

CROSS REFERENCE TO RELATED APPLICATIONS

This application claims the benefit of priority under 35 U.S.C. § 119 of German Application 10 2023 124 033.1, filed Sep. 6, 2023, the entire contents of which are incorporated herein by reference.

TECHNICAL FIELD

The invention relates to a process and a system for automated fluid balancing for a patient.

SUMMARY

It is an object of the invention to provide a process and a system which can be used during the care of a patient lying in a bed. The process and the system are intended to reduce the risk of the patient suffering damage to his or her health.

The problem is solved by a process with features according to the invention and by a system with features according to the invention. Advantageous embodiments are disclosed. Advantageous embodiments of the process according to the invention are, if appropriate, also advantageous embodiments of the system according to the invention and vice versa.

The process according to the invention and the system according to the invention are capable of automatically performing a fluid balance for a patient and thereby providing a fluid balance for the patient. The process according to the invention is carried out using the system according to the invention.

A reference time period is predefined which has a length of 24 hours, for example. The fluid balance calculated according to the invention is the difference between the total amount of fluid supplied to the patient during the reference time period and the total amount of fluid leaving (discharged from) the patient during this reference time period. The amount is preferably given as a mass. The total amount of fluid supplied to the patient in the reference time period also includes the fluid that the patient actively ingests, for example by drinking from a drinking vessel. The total amount of fluid leaving the patient during the reference time period also includes the fluid that the patient sweats out or actively excretes outside the bed.

If the difference and therefore the fluid balance is greater than zero, the patient has taken in fluid during the reference time period on balance, otherwise the patient has given out fluid on balance.

The patient lies in bed continuously or at least temporarily during the reference time period. At least one moveable object is used to care for the patient, or at least one moveable object can be used. Moveable means that the object can be moved during the care of the patient and relative to the patient. The object or at least one, preferably each object that is used or can be used is provided with a machine-readable marking (label, identification, indicia). This marking distinguishes the object from another object or from each other object used, or at least from each different object. At the very least, however, each used or usable object that can hold and provide a fluid is provided with a machine-readable marking.

The marking of an object is stored on an NFC tag, for example, whereby the NFC tag takes the form of an RFID tag, e.g. Alternatively, the marking may take the form of a bar code or QR code on the object. The marking can also comprise a sequence of alphanumeric characters and/or at least one symbol. The marking can also comprise several components. The marking may also include the contour and/or the color or at least one color of the object.

A computer-evaluable objects list is predefined (given). This objects list is stored in a system data memory, for example. It comprises an entry for each used or usable marked object. The entry comprises information about the machine-readable marking of the object and at least one of the following pieces of information:

- information about the weight of the object,
- information about the amount of fluid that this object can hold.

It is possible that the entry about an object with a marking includes the information that this object is not able to hold fluid.

The system according to the invention comprises a reading unit with at least one reader (reading device) and a camera unit with at least one camera (image acquisition device). Each reader has a respective reading area. The reader is able to read a machine-readable marking when the marking is located in the reading area. Each camera has a respective field of view (field of vision). The bed is located in the respective reading area of each reader and in the respective field of view of each camera during the reference time period. Preferably, neither the bed nor a reader nor a camera is moved during the reference time period, in particular not moved with respect to each other.

The camera or each camera is capable of generating at least one image, preferably a sequence of images. These images show the bed, optionally the patient in the bed and optionally the object or each object and the person or each person, provided that this object and/or this person are in the camera's field of view. The camera is capable of generating a signal, this signal comprising the generated image or sequence of images. The reader or each reader is capable of reading the respective machine-readable marking of an object in the reading area of the reader and generating a signal comprising the reading result.

The system according to the invention also comprises a bed scale. The bed scale is capable of measuring the current weight of the bed. If the patient is in bed at the time of measurement, the measured weight includes the weight of the patient in addition to the weight of the bed including the weight of optional bedding. The measured weight can be used to clearly determine whether the patient is in bed at the time of measurement or whether the bed is empty at the time of measurement.

A signal processing unit of the system has at least temporary read access to the objects list. The signal processing unit can be a component of a portable computer, for example a smartphone or a tablet, or a component of a stationary computer, for example a PC.

The respective signal of the reader or each reader and of the camera or each camera is transmitted to the signal processing unit, preferably wirelessly by radio waves, alternatively by means of a data cable. The signal processing unit processes the received signals.

The process according to the invention comprises the following steps, and the system according to the invention is configured to perform the following steps:

The bed scale repeatedly measures the current weight of the bed during the reference time period. The signal processing unit determines a first time point and a subsequent second time point, whereby the bed scale has measured the current weight of the bed at both time points and the patient is lying in bed at both time points. Preferably, the first time point is in the first third, particularly preferably in the first eighth of the reference time period, and the second point in time is in the last third, particularly preferably in the last eighth of the reference time period. Preferably, the bed scale measures the current weight at least three times during the reference time period, particularly preferably at a fixed sampling rate.

The signal processing unit derives at least one weight difference. The weight difference or a weight difference is the difference between the weight of the patient at the second point in time and the weight of the patient at the first point in time-more general; the difference between the weight at an earlier time point and the weight at a later time point. This weight difference does not depend on the weight of the bed, because the bed scale weighs the weight of the bed at both the first and second time points, and the patient is in bed at both the first and second time points.

The reading unit reads the respective marking of an object in the reading area of a reader. The camera unit generates at least one image, preferably a sequence of images, whereby the image or each image shows at least the bed, as well as every moveable object and every person who comes into the vicinity of the bed and thus into the field of view of a camera of the camera unit.

The signal processing unit detects any object that comes into the vicinity of the patient and/or is removed from the vicinity of the patient in the reference time period and therefore comes into the respective reading area of at least one reader and/or into the field of view of at least one camera. For this detection, the signal processing unit uses the signal of a reader or each signal of the readers and the signal of a camera or each signal of the cameras.

It is possible that the signal processing unit identifies and detects an object both on the basis of a signal from the reading unit and on the basis of a signal from the camera. For example, the reading unit reads a machine-readable marking, and image processing identifies an optically detectable marking of the same object in an image from the camera.

The signal processing unit calculates a fluid balance for the patient. The term fluid balance has already been defined above. The fluid balance refers to the given reference time. To calculate the fluid balance, the signal processing unit uses

- the derived weight difference,
- information on which objects were brought into the vicinity of the bed during the reference time period,
- information on which objects were removed from the vicinity of the bed and, if so, which objects were removed from the vicinity of the bed during the reference time period, and
- the fluid quantities and/or weights according to the objects list.

The signal processing unit determines which objects came into the vicinity of the bed and which objects were removed again based on a signal from the reading unit and/or a signal from the camera unit.

For each used or usable object and therefore also for each detected object, the objects list contains information about the empty weight of this object and/or the amount of fluid that this object can hold.

The process according to the invention and the system according to the invention can be used for a patient, in particular while the patient is in a hospital, in a care facility or at home and while the patient is receiving medical care and/or nursing care. The patient may suffer damage to his/her health if he/she does not drink enough fluids within the reference time period. The fluid supplied should at least replace the fluid discharged to a sufficient extent. If the fluid balance is negative and less than a predefined lower threshold, there is a risk that the patient will become dehydrated. Dehydration (exsiccosis) can lead to the patient's water and electrolyte balance being disturbed and the patient's health suffering as a result. If, on the other hand, the fluid balance is positive and greater than a predefined upper threshold, there is a risk of fluid settling in the patient's tissue and oedema developing, which is also undesirable.

The fluid balance for the patient in the reference time period is influenced by different influencing variables. Because the system according to the invention comprises different sensors and the objects list and the process according to the invention processes signals from these sensors and the objects list, many of these different influences can be quantitatively determined in order to calculate the fluid balance.

The invention can be used in conjunction with the step of weighing the patient outside the bed, in particular immediately before the reference time period and/or immediately after the reference time period. It is possible to determine the difference between these two patient weights. However, the invention eliminates the need to weigh the patient outside the bed. Especially in everyday clinical practice, there is often a lack of staff and time for this. In addition, the invention makes it possible to install and connect the components of the system according to the invention once for a patient and then to calculate the fluid balance repeatedly for different periods of time, even for different patients, without human intervention being required for the calculation. In addition, it is often not sufficient for providing a reliable fluid balance if the patient is weighed once before and once after the reference time period.

According to the invention, a reading unit and a camera unit are used. In particular, this feature enables the signal processing unit to recognize which objects come into the vicinity of the bed and thus into the vicinity of the patient in the bed and which objects are removed from the bed and thus from the patient. From the objects list, the signal processing unit obtains information on the amount of fluid that each object is capable of holding and is therefore supplied to the patient when the object comes into the vicinity of the patient. It is also often possible to determine whether or not an object containing fluid is actually brought to the patient's mouth. The objects list also makes it possible to distinguish between the process of delivering fluid to a patient and the process of using an object near the patient without delivering fluid to the patient, such as a cutlery set or a book or even a medical instrument.

In one embodiment, the bed scale measures the current weight of the bed more than twice during the reference time period, preferably at a predefined sampling rate. The signal processing unit determines a time (temporal) course of the weight of the bed, for which it receives and processes a signal from the bed scale. The signal processing unit uses the time course of the bed weight to calculate the fluid balance for the patient. The determined time course of the bed weight covers at least a time span between the first time point and the second time point, optionally the entire reference time period.

Thanks to this embodiment, the signal processing unit is in many cases able to determine with greater certainty the amount of fluid the patient has consumed (taken in) while lying in the bed. By processing signals from the reading unit and from the camera unit, the signal processing unit detects the event that an object is brought to the patient's body and later removed again, or determines that such an event has not occurred. By evaluating the objects list, the signal processing unit recognizes the amount of fluid this object is able to hold and/or what this object weighs without fluid (empty weight). The time course of the bed weight provides information on how the measured weight of the bed with the patient and therefore the patient's weight has changed. This information is always available in connection with the respective times of measurement or detection. The signal processing unit uses this information to determine how much fluid the patient has actually consumed. Thanks to the signals from the reading unit and the camera unit, this situation can be distinguished from a situation in which the patient picks up an object in bed or an object is brought to or into the bed without the patient ingesting fluid.

In a further development of this embodiment, the signal processing unit automatically searches for an exit time point, a subsequent return time point and a third time point between these two time point. The signal processing unit carries out the search in such a way that these three time points cumulatively have the following properties:

All three time points are within the reference time period.

The current weight of the bed was measured at all three time points.

The patient was in bed at the exit time point and at the return time point.

At the third time point, the patient was out of bed.

In particular the signal processing unit uses the time points, and the first time point is the exit time point and the second time point is the return time point.

As already mentioned, the signal processing unit uses a measured value from the bed scale to determine whether the patient was inside or outside of the bed at the time of measurement. It is possible, but thanks to the bed scale not necessary, that an additional sensor is used for this determination.

If the signal processing unit has found three such time points, it performs the following steps:

The signal processing unit calculates the difference between the measured weight of the bed at the exit time and the measured weight of the bed at the return time.

The signal processing unit uses the calculated difference to calculate the fluid balance.

At the third time point, i.e. in the time span between the exit time point and the return time point, the patient may have excreted fluid outside the bed, for example on a toilet, but may also have consumed fluid outside the bed. The measured difference approximates the balance between fluid output and fluid intake in the time span between the exit and return time points. This configuration can be used in combination with the process of weighing the patient at least once outside the bed. Thanks to this further development, however, it is not necessary to weigh the patient during the out-of-bed time span.

In one embodiment, the system comprises at least one volume flow sensor. The volume flow sensor is able to measure the volume flow of a fluid through a fluid guide unit, alternatively or additionally the mass flow of the fluid. More specifically, the volume flow sensor directly measures the volume flow or the mass flow or a variable that correlates with the volume flow and/or with the mass flow.

According to the embodiment, the volume flow sensor measures the volume flow or mass flow of a fluid through a fluid guide unit while this fluid guide unit is connected to the patient's body. The fluid can flow through the fluid guide unit into the patient's body or flow out of the patient's body through the fluid guide unit. It is possible for a fluid to flow into the patient's body through a fluid guide unit and for the same or another fluid to flow out of the patient's body and through another fluid guide unit. For example, an infusion solution flows from a bag into the patient's body through the fluid guide unit, and urine flows out of the body and into a urine bag. At least in a time span between the first time point and the second time point the fluid guide unit is connected with the patient's body. The volume flow or the mass flow is measured at least in this time span, In one embodiment, a fluid guide unit is used in such a way that fluid flows through the fluid guide unit in two opposite directions in succession. Preferably in this case, the volume flow sensor also determines the current flow direction. The signal processing unit receives a signal from the volume flow sensor and uses the measured volume flow to calculate the fluid balance.

This embodiment further improves the accuracy and reliability with which the fluid balance is calculated according to the invention.

Notes:

A fluid guide unit is understood to be a component that is able to guide a fluid along a trajectory, whereby the trajectory is predefined by the configuration and arrangement of the component. For example, the fluid guide unit comprises a tube and a hose.

The volume flow is understood to be the volume that flows through a fluid guide unit per unit of time. The mass flow is understood to be the mass that flows through the fluid guide unit per unit of time. The fluids that the patient absorbs or releases during the reference time period generally have a high proportion of water and therefore a specific density that is approximately equal to the specific density of water. The volume flow is therefore approximately proportional to the mass flow.

In one embodiment, the system according to the invention comprises a urine bag scale. This urine bag is connected to the patient at least temporarily during the reference time period. The patient releases urine into the urine bag by means of a tube and preferably by means of a catheter. The signal processing unit determines a time course of weight of the urine bag and processes a signal from the urine bag scale for this purpose. The time course is measured at least in a time span between the first time point and the second time point. The signal processing unit uses the time course to calculate the fluid balance.

According to this embodiment, the signal processing unit processes the time course of the weight of the urine bag. This enables the signal processing unit to determine the volume flow or mass flow into the urine bag on the one hand. On the other hand, it is able to detect the event that the urine bag is replaced or emptied. This process usually leads to a sudden change in the measured weight of the urine bag.

In one embodiment, the system according to the invention comprises a table scale. The table scale is able to measure the weight of a table. During the reference time period, this table is at least temporarily in the vicinity of the patient. The table can stand on a floor or be connected to the bed. Objects that are used or can be used for the care of the patient can be placed on this table. Some of these objects may contain fluids, such as drinks or solid food. The signal processing unit determines a time course of a weight of the table. For doing so, the signal processing unit processes a signal from the table scale. The time course covers at least a time span between the first time point and the second time point. The signal processing unit uses the determined time course to calculate the fluid balance.

Thanks to this embodiment, the signal processing unit is in particular able to detect the process of a container with fluid being placed on the table, emptied step by step and then removed from the table again. Preferably, the signal processing unit also detects this container using the signals from the reading unit and/or the camera unit. By reading access to the objects list, the signal processing unit determines how much this container weighs and/or how much fluid this container can hold. Because different pieces of information are combined, the reliability with which the amount of fluid is calculated increases, whereby the patient consumes this amount of fluid from the container.

According to the invention, the reading unit comprises at least one reader. The camera unit comprises at least one camera. In one embodiment, the reading unit comprises at least two readers and/or the camera unit comprises at least two cameras. Preferably, the reading directions of the readers differ from one another, and the viewing directions of the cameras also differ from one another. The signal processing unit determines the respective movement of each object relative to the bed during the reference time period and additionally identifies this object by means of the marking. In particular, this feature enables the signal processing unit to decide in many cases whether fluid in this object is being brought to the patient and/or fluid is being discharged from the patient and/or neither fluid is brought to the patient nor fluid is discharged from the patient. The signal processing unit uses each determined relative movement to calculate the fluid balance.

The patient usually consumes fluid from a container at least once during the reference time period. This container is configured to hold a drinkable fluid and to be brought to the patient's mouth. For example, the container is placed on a support surface of a patient table and the patient takes the container and drinks from it. Or the container is held in front of the patient's mouth. According to the invention, this container is also provided with a unique machine-readable marking. The weight of the container and/or the amount of fluid that the container can hold is stored in the objects list.

With the following configuration, the amount of fluid that the patient drinks from a container during the reference time period is taken into account in the fluid balance with a relatively high degree of reliability. The signal processing unit performs the following sequence at least once:

The signal processing unit detects the event that the container is brought to the patient's mouth.

It determines how long the patient drinks from this container.

It determines an approximate value (an indicator) for the amount of fluid that the patient consumes from this container.

It uses this approximate value to calculate the fluid balance.

For this detection and determination, the signal processing unit uses at least one signal from the reading unit, at least one signal from the camera unit, and the objects list.

Thanks to the machine-readable markings and the camera unit, the movement of an object relative to the patient's bed can be easily tracked. Therefore, the signal processing unit is able to detect that an object in the shape of a container is brought to the patient's mouth. Furthermore, the signal processing unit is able to detect the events that fluid is spilled or that the patient brings the container to the mouth but does not drink.

The following embodiment takes into account the possibility that the patient excretes fluid while lying in bed and this fluid is absorbed by textiles, whereby these textiles are located in the bed and there between the patient and the bed or on the patient's body. The textiles include, in particular, a bed pad or the patient's clothing. For example, the patient sweats out fluid. Because this fluid remains in the bed, it does not lead to a change in the weight measured by the bed scale or the optional table scale.

According to this embodiment, the signal processing unit is configured to detect the event that the used object is replaced by a fresh object, for example that the patient's bedding and/or clothing are changed. For this detection, the signal processing unit uses a signal from the reading unit and/or a signal from the camera unit.

Before the replacement, the object has absorbed moisture that the patient has excreted into the bed. As a rule, the fresh object is of the same type as the replaced object, but fresh and therefore dry. The difference between the weight of the used object and the weight of the fresh object is therefore approximately equal to the weight of the fluid that the patient has released into the used and then replaced object in bed. It is possible that the weight of the used object before replacement and the weight of the fresh object are measured. Thanks to the following implementation, however, the need to measure the weight of this object separately is avoided.

According to this implementation, the weight of the bed is measured on the one hand at a time before the replacement, i.e. at a time when the old object, which may have absorbed fluid, is still in the bed. On the other hand, the weight of the bed is measured after the replacement, i.e. at a time when the fresh object is in the bed, i.e. an object that has not yet absorbed a significant amount of fluid from the patient. Either the patient is in bed at these two time points, or the patient is out of bed at these two time points. As already explained, the signal processing unit can clearly decide whether the patient was in bed or out of bed at the time of measurement based on the weight measured by the bed scale at the time of measurement. The measured weight of the bed before the replacement minus the measured weight of the bed after the replacement provides an approximation of the weight of the fluid that the patient released into the object before the replacement.

Another implementation does not necessarily require that the object that receives or can receive fluid from the patient is replaced in the reference time period and that this replacement is detected. According to this other implementation, the signal processing unit detects two time points in the reference time period, whereby the current weight of the bed has been measured at these two time points and the patient was not in the bed. The signal processing unit calculates the difference between the bed weight at the later time point and the bed weight at the earlier time point. In many cases, this difference corresponds sufficiently accurately to the amount of fluid that the patient excreted into the bed between the earlier and later time points.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
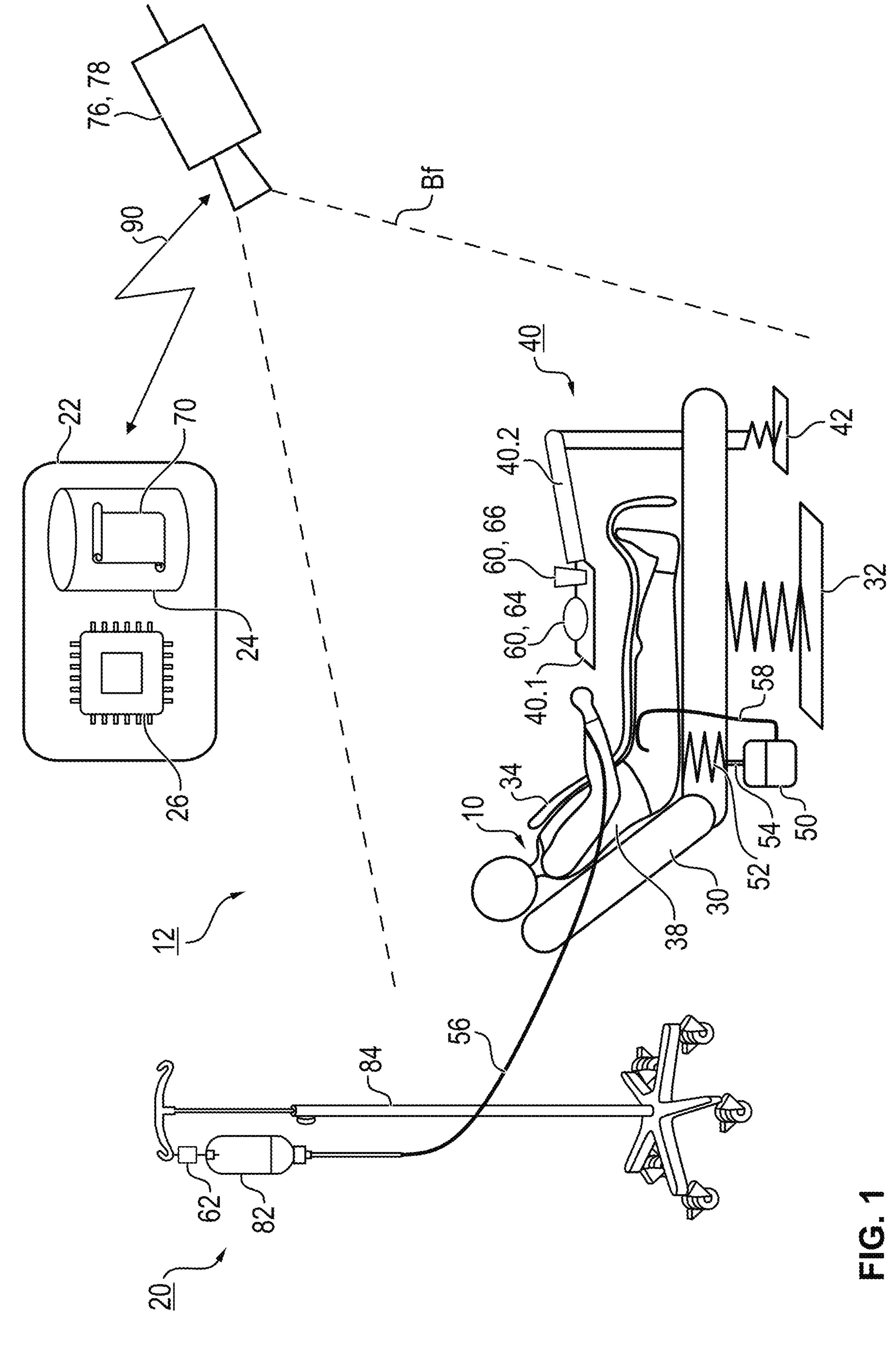
FIG. 1 is a schematic view of a patient in a patient bed, various objects for the care of the patient and the fluid balancing system according to the invention.
Figure 2:
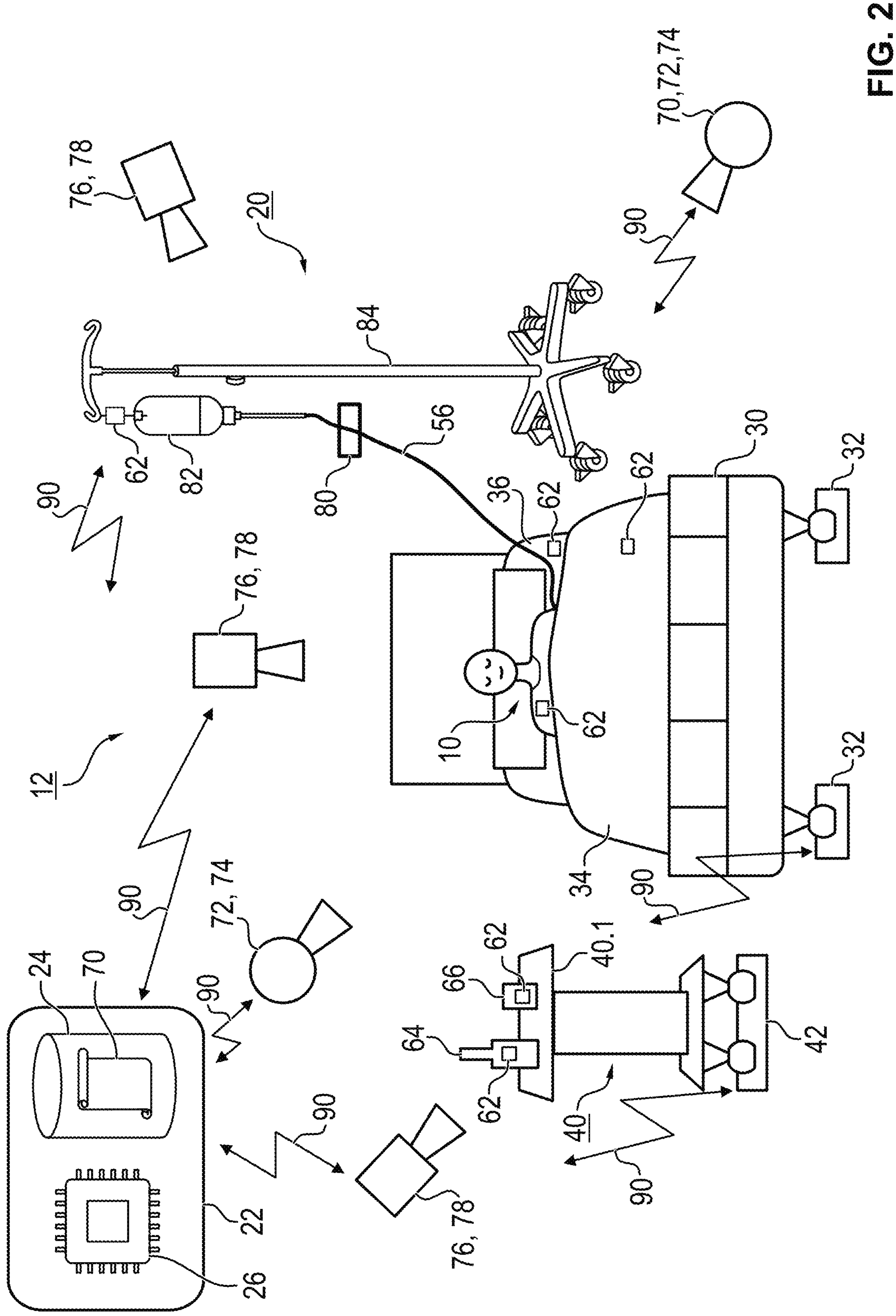
FIG. 2 is a schematic view of the patient and the objects in FIG. 1 from a different viewing direction.

Referring to the drawings, FIG. 1 and FIG. 2 schematically show a fluid balancing system 20 according to the invention. Identical reference signs have the same meanings.

Application Example

The fluid balancing system 20 is used to determine a fluid balance for a patient 10. The fluid balance relates to a reference time period T and is the difference between the total amount of fluid supplied to the patient 10 in the reference time period T and the total amount of fluid leaving the patient 10 in the reference time period T. The reference time period T has a length of 24 hours, for example.

During the reference time period T, the patient 10 lies continuously or at least temporarily in a bed, in this case in a patient bed 30, which is located in a room 12 of a hospital. During the reference time period T, the patient bed 30 remains in place. It is possible for the patient 10 to temporarily leave the patient bed 30. The bed can also be a normal sleeping bed or a couch and be located in a room of an apartment.

The patient 10 is wearing clothing 38 while lying in the patient bed 30. The patient 10 is covered with bedding 34 or is lying on bedding 34, the bedding 34 including, for example, a comforter (duvet) and a pillow. There is also a bed pad 36 between the patient 10 and the patient bed 34.

Next to the patient bed 30 is a patient table 40 on which objects can be placed. The patient table 40 comprises a storage surface 40.1, an articulated support arm 40.2 and a stand. In addition, next to the patient bed 30 is a mobile holding device 84 in the manner of a mobile clothes rack, on which an infusion bag 82 hangs. During the reference time period T, a tube (hose) 56 connects the infusion bag 82 to the body of the patient 10, either continuously or at least temporarily. A fluid from the infusion bag 82 flows through the tube 56 into the body of the patient 10. A holding device 54 on the patient bed 30 holds a urine bag 50. A tube 58 connects the body of the patient 10 to the urine bag 50, continuously or at least temporarily.

Components of the Fluid Balancing System

The fluid balancing system 20 of the embodiment example comprises

- a bed scale 32,
- a table scale 42,
- a urine bag scale 52 and
- a volume flow sensor 80.

The bed scale 32 is able to measure the weight of the patient bed 30. In the embodiment example, the patient bed 30 is placed on an external bed scale 32. When the patient 10 is lying in the patient bed 30, the bed scale 32 measures the sum of the weight of the patient bed 30 and the weight of the patient 10. When the patient 10 has left the patient bed 30, the bed scale 32 measures the weight of the empty patient bed 30.

The table scale 42 is able to measure the weight of the patient table 40. In the embodiment example, the patient table 40 stands on the table scale 42. If there is at least one object on the storage surface of the patient table 40, the table scale 42 additionally measures the weight of the object or each object on the storage surface.

The urine bag scale 52 is able to measure the weight Gew (50) of the urine bag 50. The volume flow sensor 80 measures the volume flow Vol' (56) or the mass flow from the infusion bag 82 through the tube 56. It is possible that fluid is supplied to the body of the patient 10 from another container or device, or fluid is aspirated or otherwise discharged, and the corresponding volume flow or mass flow is also measured. The corresponding sensor may be a component of the device. The sensors 32, 42, 52 and 80 measure the respective physical quantity repeatedly, preferably at a fixed sampling frequency.

Several moveable objects 60 are used to care for the patient 10 while he or she is lying in the patient bed 30. By way of example, the moveable objects 60 shown are a drinking bottle 64, a cup 66, the bedding 34, the bed pad 36 and the clothing 38 of the patient 10.

At least one, preferably each, object 60 is provided with a respective machine-readable marking 62, but at least each object which can receive fluid is provided with a respective machine-readable marking 62. This marking 62 distinguishes this object 60 from any other, or at least from any different, object used to care for the patient 10. Different examples of the same object 60 may therefore have the same marking 62. For example, the marking 62 takes the form of an RFID tag, a bar code, a QR code, a particular pattern or symbol, or a sequence of alphanumeric characters. The color and/or the contour of the object 60 can also be used alone or as a color-contour combination as the marking 62. Preferably, the marking 62 is applied to an object several times (at several locations on the respective object) so that at least one marking 62 can be read.

The fluid balancing system 20 comprises a reading unit 72 having at least one reader 74, preferably a plurality of readers 74, and a camera unit 76 having at least one camera 78, preferably a plurality of cameras 78. The reader or each reader 74 has a reading area. The camera or each camera 78 has a field of view Bf with a central viewing direction (viewing axis). Preferably, the fields of view differ from one another, and at least two directions of view are arranged at an angle to one another.

Preferably, each reader 74 and each camera 78 is fixedly mounted, for example on a ceiling or a wall of the room 12 or on the patient table 40 or on the patient bed 30. The reader 74 and the camera 78 therefore maintain their position relative to the patient bed 30 during the reference time period T. During the reference time period T, the patient bed 30 is therefore continuously located in the reading area or each reading area and in the field of view or each field of view.

The reader or each reader 74 is capable of reading or otherwise detecting the respective marking 62 of each object in the reading area of the reader 74. Read (62) refers to a read result of the reader 74. Preferably, the reader 74 repeatedly scans the marking 62 at a scanning frequency. The camera or each camera 78 is capable of capturing one image Abb(60) at a time, preferably a sequence of images at a sampling rate. Each reader 74 and each camera 78 generates a signal with the respective read result Read (62) or the respective image Abb(60) or the sequence of images. The image Abb(60) of a camera 78 therefore shows

- the patient bed 30,
- the patient 10 when the patient 10 is in the patient bed 30, and
- any person or object 60 near the patient's bed 30.

The fluid balancing system 20 further comprises a signal processing unit 22 with a data memory 24 and a processor 26. The processor 26 has at least temporary read access to the data memory 24 and executes a stored program. The signal processing unit 22 can be a component of a smartphone or tablet or other portable computer.

Functionality of the Fluid Balancing System

Figure 3:
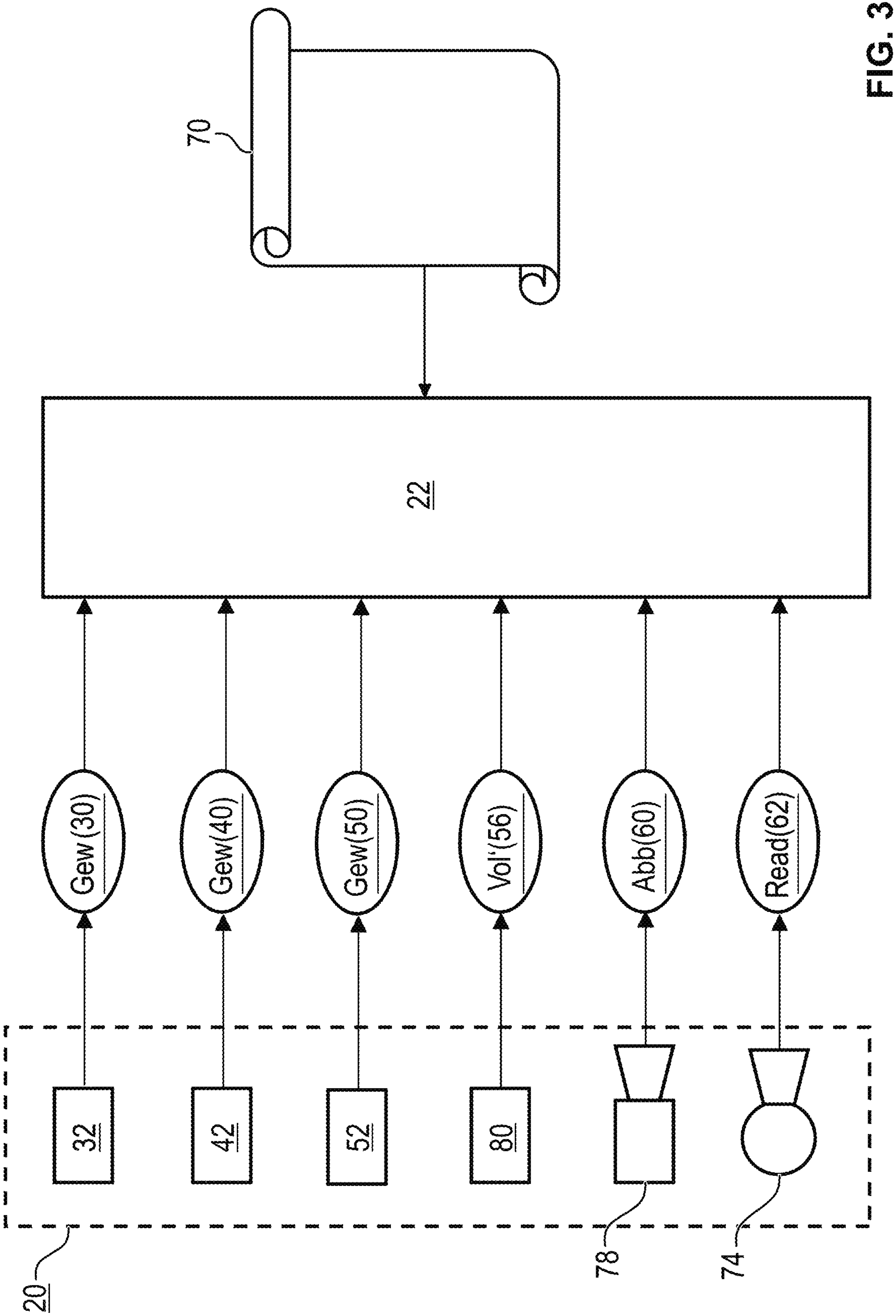
FIG. 3 is a schematic view showing signal connections including which signals and other information the signal processing unit processes in order to calculate the fluid balance.

The signals just described are transmitted to the signal processing unit 22, preferably wirelessly via electromagnetic radio waves 90. FIG. 3 shows an example of the signals and other information received and processed by the signal processing unit 22.

The signal processing unit 22 receives a signal from each reader 74 and each camera 78 and processes the received signals. By evaluating the signal from a reader 74, the signal processing unit 22 detects and identifies each machine-readable marking 62 in the reading area of the reader 74 and thereby detects and identifies the marked object 60. Optionally, the signal processing unit 22 determines how an object 60 with a particular marking 62 moves relative to the patient bed 30 based on a varying field strength of the signal from the reader 74. An image processing unit of the signal processing unit 22 processes the signal from a camera 78 and thereby detects each person and each object in the field of view of the camera 78.

In one embodiment, the image processing unit applies a classifier. This classifier detects and classifies objects in an image Abb(60) of the camera 78. Preferably, the classifier is trained in advance with a random sample, for which a machine learning process is used. The classifier is implemented, for example, as a neural network. The configuration with the classifier creates redundancy and increases the reliability that a movement of an object 60 is correctly detected: An object 60 can be classified on the one hand on the basis of its marking 62 and on the other hand on the basis of its contour.

Overall, the signal processing unit 22 uses the classification to determine the respective position and movement of each object 60 having a marking 62 relative to the patient bed 30 and thus relative to the patient 10. In addition, the signal processing unit 22 determines whether an object 60 has been at the mouth of the patient 10 for a sufficiently long time span. If this object 60 is the drinking bottle 64 or the cup 66, this detection is an indication that the patient 10 is ingesting fluid from this object 60 or spilling fluid. This distinction cannot be made reliably simply by evaluating a signal from a scale.

In addition, the signal processing unit 22 receives a signal from each of the bed scale 32, the table scale 42, the urine bag scale 52 and the volume flow sensor 80, preferably also wirelessly via radio waves 90. In the embodiment example, the signal processing unit 22 determines the following time courses in the reference time period T:

- the time course of the weight of the patient bed 30, whereby if the patient 10 is lying in the patient bed 30, the measured weight includes the weight of the patient 10, otherwise only the measured weight of the patient bed 30 including the bedding and the bed pad,
- the time course of the weight of the patient table 40, wherein, if at least one object 60 is on the patient table 40, the measured weight comprises the weight of this object 60,
- the time course of the weight of the urine bag 50 and
- the time course of the volume flow through the tube 56.

The signal processing unit 22 preferably compensates for short-term oscillations over time by calculation. Such oscillations are caused by short-term and small movements of the patient 10 or a caregiver or even an external vibration source and do not significantly affect the fluid balance. For example, the signal processing unit 22 applies a low-pass filter to the signal from the sensor 32, 42, 52, 80.

At least temporarily, the signal processing unit 22 has read access to a computer-evaluable objects list 70. For example, the objects list 70 is stored in the data memory 24. This objects list 70 contains an entry for each object 60 that is detectable on the basis of a marking 62 and/or by the optional classifier described above. This entry contains

- information on the marking 62 and
- information about the weight of the object 60 and
- information about the mass and volume of fluid that this object 60 can hold.

In the case of a drinking vessel as object 60, the information includes, for example, information about the volume and/or the empty weight of the drinking vessel. It is of course possible that the object cannot hold fluid or is not used to hold fluid. If the object is a plate or a bowl and can hold food, the objects list comprises information about the average amount of fluid contained in the solid food consumed.

Calculation and Evaluation of the Fluid Balance

The signal processing unit 22 calculates a fluid balance for the patient 10. In the embodiment example, this fluid balance is the mass or also the volume of fluid that has been supplied to the patient 10 in total in the reference time period T, minus the mass or also the volume of fluid that the patient 10 has discharged in total in the reference time period T.

The calculated fluid balance can be positive or negative. If the fluid balance is positive, the patient has consumed (taken in) more fluid on balance in the reference time period T than he or she has excreted. Otherwise, he or she has excreted more fluid than he or she has consumed. In one embodiment, a value range with an upper threshold and optionally a lower threshold is predefined. The upper threshold is greater than zero, the lower threshold is less than zero. The fluid balance in the reference time period T for patient 10 should lie within this range of values. If the fluid balance is less than the lower threshold, then patient 10 has consumed too little fluid in the reference time period T. There is then a risk that patient 10 will become dehydrated. If the fluid balance is greater than the optional upper threshold, there is a risk that fluid will be deposited in the tissue of the patient 10, which is also undesirable.

Preferably, the signal processing unit 22 checks whether the fluid balance for the reference time period T is within the range of values or whether it is less than the lower threshold or greater than the upper threshold. If the fluid balance is outside the range of values, the signal processing unit 22 generates a corresponding message and causes this message to be output in at least one form that can be perceived by a human, preferably by a receiver outside the room 12. Preferably, the message indicates whether the patient has consumed too much or too little fluid. In one embodiment, a corresponding message is also generated and output if the fluid balance is within the value range. A fluid balance far outside the value range can still be an indication that the fluid intake or a fluid intake was not detected or that a device in the system is operating incorrectly.

Patient 10 consumes (takes in) fluids, in particular through the following actions:

- A fluid is supplied to the patient 10 from the infusion bag 82 and through the tube 56. This supply causes a volume flow and a mass flow through the tube 56, and the volume flow sensor 80 measures this volume flow or this mass flow.

A drinking vessel, for example the drinking bottle 64 and/or the cup 66, is placed on the patient table 40—more precisely: on a support surface of the patient table 40. The patient 10 grasps the drinking vessel 64, 66, drinks from the drinking vessel 64, 66 and places the completely or at least partially emptied drinking vessel 64, 66 back on the patient table 40. The drinking vessel 64, 66 on the patient table 40 contributes to the measured weight of the patient table 40. The table scale 42 continuously measures the weight of the patient table 40. If the patient 10 holds the drinking vessel 64, 66 in one hand, the weight contributes to the weight measured by the bed scale 32. Preferably, the signal processing unit 22 compares the time course of the weight of the patient bed 30 with the time course of the weight of the patient table 40 to determine whether the patient 10 is actually ingesting fluid from a drinking vessel 64, 66 that was previously on the patient table 40.

A caregiver (not shown) holds the drinking vessel 64, 66 to the mouth of the patient 10, and the patient 10 drinks from the drinking vessel 64, 66 without placing the drinking vessel 64, 66 on the patient table 40. Drinking increases the weight of the patient bed 30.

In particular, the patient 10 discharges (releases) fluid through the following actions:

Urine flows from the body of the patient 10 through the tube 58 into the urine bag 50. The urine bag scale 52 measures the weight of the urine bag 50, and the signal processing unit 22 determines a time course of the urine bag weight. If the measured weight suddenly decreases, the urine bag 50 has been replaced by a new empty urine bag, and the signal processing unit 22 takes this into account.

The patient 10 leaves the patient bed 30 and defecates on a toilet. Using a signal from the bed scale 32, the signal processing unit 22 determines the weight of the patient 10 before he or she has left the patient bed and the weight after he or she has returned to the patient bed 30. The difference in weight corresponds approximately to the amount of fluid excreted.

The patient 10 releases fluid onto the clothing 38 or the bed pad 36, for example because the patient 10 sweats out fluid. The amount of fluid released by the patient 10 in this way can be approximately determined when worn clothing 38 or a used bed pad 36 is replaced by fresh clothing 38 or a fresh bed pad 36. The difference between the weight of the used clothing/bed pad and the fresh clothing/bed pad approximately indicates the amount of fluid dispensed. This difference is derived, for example, from the following difference: the weight of the patient bed 30 with the patient 10 before the replacement of objects minus the weight of the patient bed 30 with the patient 10 after the replacement of these objects. In many cases, the image processing unit is able to detect the event that the clothing 38 and/or the bed pad 36 are replaced.

The following events do not usually affect the fluid balance:

Cutlery or a book or any other object that does not hold fluid is placed on the patient table 40 or removed from the patient table 40.

Note: Because the signal processing unit 22 determines time courses and derives differences from them, the weight of the empty patient bed 30 or the weight of the empty patient table 40 is not necessarily required.

In the embodiment example, the possibility that objects are placed on the patient table 40 and/or removed from the patient table 40 one after the other or simultaneously is taken into account. Each object changes the weight of the patient table 40, and the table scale 42 weighs this weight. The weight of the object on the patient table 40 thus influences the time course of the weight of the patient table 40, whereby the signal processing unit 22 determines this time course as described above. The signal processing unit 22 also identifies each object 60 that is placed on the patient table 40 or removed from the patient table 40 by means of the marking 62, at least if this object 60 is capable of receiving fluid. By reading the objects list 70, the signal processing unit 22 determines how much fluid an identified object 60 is capable of holding. The signal processing unit 22 determines how much fluid the patient 10 has consumed in total from objects placed on the patient table 40 in the reference time period T. For this purpose, the signal processing unit 22 uses the determined time course of the weight of the patient table 40 and the amount of fluid that an identified object 60 on the patient table 40 can hold according to the objects list 70. In particular, the signal processing unit 22 determines that an object changes the weight of the patient table 40 but does not hold any fluid and therefore does not contribute to the fluid balance, for example cutlery or a book. If an object 60 does not bear a marking, this object is preferably disregarded when calculating the fluid balance. In addition, the signal processing unit 22 optionally determines the event that the patient 10 spills fluid from an identified drinking vessel 60 and takes this approximately into account when calculating the fluid balance.

It is possible that a full drinking vessel, for example the drinking bottle 64 or the cup 66, was placed on the patient table 40 before drinking and the empty drinking vessel is placed back on the patient table 40 after drinking. This changes the measured weight of the patient table 40. Consideration is given to the possibility that a caregiver holds a drinking vessel 64, 66 in front of the mouth of the patient 10 and the patient 10 drinks from the drinking vessel 64, 66 without placing the drinking vessel 64, 66 on the patient table 40. In this case, the drinking vessel 64, 66 does not change the measured weight of the patient table 40.

The image processing unit of the signal processing unit 22 detects the event that a drinking vessel 64, 66 is brought to the mouth of the patient 10 and the event that the drinking vessel 64, 66 is moved away from the mouth of the patient 10 again. The signal processing unit 22 identifies the drinking vessel 64, 66 by means of the marking 62 and determines by image evaluation that this drinking vessel 64, 66 is located in front of the mouth of the patient 10. The signal processing unit 22 determines how much fluid this drinking vessel is capable of holding by reading access to the objects list 70. Preferably, the signal processing unit 22 uses the assumption that the patient 10 ingests this amount of fluid while the drinking vessel 64, 66 is held in front of his/her mouth.

In one embodiment, the possibility is taken into account that fluid from a drinking vessel 64, 66 does not enter the body of the patient 10, but is poured out or spilled. This event can also be detected by the image evaluation unit and the amount of fluid spilled can be approximately determined from the movement of the drinking vessel 64, 66.

While specific embodiments of the invention have been shown and described in detail to illustrate the application of the principles of the invention, it will be understood that the invention may be embodied otherwise without departing from such principles.

| List of reference characters | |
|---|---|
| 10 | Patient, lying in patient bed 30 |
| 12 | Hospital room in which patient bed 30 with patient 10 is located |
| 20 | Fluid balancing system according to the invention |
| 22 | Signal processing unit |
| 24 | Data memory of the signal processing unit 22 |
| 26 | Processor of the signal processing unit 22 |
| 30 | Patient bed in which the patient 10 is lying |
| 32 | Bed scale, measures the weight (30) of the patient bed 30 |
| 34 | Bedding in patient bed 30, especially comforter and pillow |
| 36 | Bed pad |
| 38 | Clothing worn by the patient 10 in the patient bed 30 |
| 40 | Patient table next to the patient bed 30, comprises the storage surface 40.1 and the articulated support arm 40.2 |
| 40.1 | Storage surface of the patient table 40 |
| 40.2 | Articulated support arm of the patient table 40 |
| 42 | Table scale, measures the weight (40) of the patient table 40 |
| 50 | Urine bag, hangs on the holding device 54 |
| 52 | Urine bag scale, measures the Gew (50) of the urine bag 50 |
| 54 | Holding device for the urine bag 50 on the patient bed 30 |
| 56 | Tube connecting the infusion bag 82 to the patient's body 10 |
| 58 | Tube connecting the patient's body 10 to the urine bag 50 |
| 60 | Moveable object used for the care of the patient 10 |
| 62 | Machine-readable marking of an object 60 |
| 64 | Drinking bottle, is an object 60 |
| 66 | Cup, is an object 60 |
| 70 | Objects list, comprises for each object 60 its marking 62 and the amount of fluid that this object 60 can hold, is stored in the data memory 24 |
| 72 | Reading unit, comprises at least one reader 74 |
| 74 | Reader, which is able to read a marking 62 information on an object 60, is directed towards the patient bed 30, generates a read result Read(62) |
| 76 | Camera unit, comprises at least one camera 78 |
| 78 | Camera, is directed at the patient bed 30, generates images Abb(60) |
| 80 | Volume flow sensor, measures the volume flow Vol'(56) or mass flow of a fluid flowing through the tube 56 |
| 82 | Infusion bag, suspended from the holding device 84, connected to the body of the patient 10 by the tube 56 |
| 84 | Holding device for the infusion bag 82 |
| 90 | Radio waves |
| Abb(60) | Image (signal) of objects 60 generated by the camera 78 |
| Bf | Field of view of the camera 78 |
| Gew(30) | Weight signal of the patient bed 30, measured by the bed scale 32 |
| Gew(40) | Weight signal of the patient table 40, measured by the table scale 42 |
| Gew(50) | Weight signal of the urine bag 50, measured by the urine bag scale 52 |
| Vol'(56) | Volumetric flow rate (signal) at which fluid flows through the tube 56, measured by the volumetric flow sensor 80 |
| Read(62) | Reading result (signal) of the reader 74 |

What is claimed is:

1. A process for fluid balancing for a patient, wherein for a care of the patient a bed is used and a moveable object or a plurality of moveable objects are used or can be used, wherein the moveable object is provided with a machine-readable marking or at least one of the moveable objects is provided with a machine-readable marking which machine-readable marking distinguishes the marked moveable object from each other used or usable moveable object, wherein a system is provided, the system comprising: a bed scale; a reading unit comprising at least one reader, a camera unit comprising at least one camera; an objects list provided in a computer-evaluable form, wherein the objects list comprises, for each moveable object, marking information for the marking for the moveable object and information about a weight of the moveable object and/or information about an amount of fluid that the moveable object is capable of taking up; and a signal processing unit, wherein a reference time period is predefined for the fluid balance, wherein the reader or each reader has a respective reading area, and the bed is located in the reading area at least during the reference time period, wherein the camera or each camera has a respective field of view, and the bed is located in the field of view at least during the reference time period, wherein the process is carried out at least in the reference time period and comprises the steps of:

with the bed scale, measuring a respective current weight of the bed at least at a first time point and at a subsequent second time point, wherein both the first time point and the second time point are within the reference time period and the patient is in the bed at both the first time point and at the second time point;

with the signal processing unit, deriving a weight difference using a signal from the bed scale, wherein the weight difference is a difference between the weight of the patient at the second time point and the weight of the patient at the first time point;

with the reading unit, reading a respective marking of at least one moveable object;

with the camera unit, generating at least one image;

with the signal processing unit, detecting each moveable object that comes into a vicinity of the patient and/or is removed from the vicinity of the patient in the reference time period, wherein the step of detecting each moveable object is performed using at least one signal of the reading unit and/or using at least one signal of the camera unit; and with the signal processing unit, calculating a fluid balance of the patient, wherein the fluid balance is a difference between a total amount of fluid supplied to the patient during the reference time period and a total amount of fluid leaving the patient during the reference time period, wherein the step of calculating the fluid balance is based on: at least one of a derived weight or each derived weight difference of the bed; information on which moveable objects have come into the vicinity of the bed and have been detected, information on which moveable objects have been removed from the vicinity of the bed and have been detected, and information on the moveable object weight and/or the moveable object quantity of fluid included in the objects list for detected moveable objects.

2. The process according to claim 1, further comprising the steps of:

with the bed scale, measuring a current weight of the bed at least once in a time span reaching from the first time point to the second time point; and with the signal processing unit, determining a time course in this time span, from the first time point to the second point time, of the weight of the bed and using the bed weight time course in the calculation of the fluid balance.

3. The process according to claim 1, further comprising the steps of:

with the bed scale, measuring a current weight of the bed at a third time point, the third time point being between the first time point and the second time point; and with the signal processing unit, checking whether the patient is outside the bed at the third time point, wherein if the patient is outside the bed at the third time point, performing the further steps of:

with the signal processing unit, using the first time point as an exit time point and the subsequent second time point as a return time point;

with the signal processing unit, determining the difference between the weight of the bed at the return time point and the weight of the bed at the exit time point as a difference between the total amount of fluid which is supplied to the patient outside of the bed and the total amount of fluid which leaves the patient outside of the bed in a time span between the exit time point and the return time point; and with the signal processing unit, using this determined weight difference for calculating the fluid balance.

4. The process according to claim 1, wherein the system further comprises a volume flow sensor, wherein a fluid guide unit is configured to be connected to the body of the patient in the time span from the first time point to the second time point;

wherein the process further comprises the steps of:

with the volume flow sensor, measuring a volume flow or mass flow of a fluid through the fluid guide unit into the body of the patient and/or out of the body of the patient; and with the signal processing unit, using the measured volume flow or mass flow to calculate the fluid balance, wherein the steps of measuring a volume flow or mass flow and using the measured volume flow or the mass flow are carried out at least in the time span from the first time point to the second time point.

5. The process according to claim 1, wherein the system further comprises a urine bag scale, and the process further comprises the steps of:

with the urine bag scale, repeatedly weighing a urine bag in the time span from the first time point to the second time point, wherein the urine bag is configured to be at least temporarily connected to the body of the patient during the time span from the first time point to the second time point;

with the signal processing unit, determining a time course of the measured weight of the urine bag during the time span from the first time point to the second time point; and using the determined urine bag weight time course in the calculation of the fluid balance.

6. The process according to claim 1, wherein the system further comprises a table scale, and the process further comprises the steps of:

with the table scale, repeatedly weighing a table in a time span from the first time point to the second time point, wherein moveable objects are placed or can be placed on the table, which moveable objects are used or can be used for the care of the patient; and with the signal processing unit, determining a time course of the measured weight of the table during the time span from the first time point to the second time point; and using the determined table weight time course in the calculation of the fluid balance.

7. The process according to claim 1, wherein the reading unit comprises at least two readers and/or the camera unit comprises at least two cameras and wherein the step of the signal processing unit detecting each moveable object comprises the steps of:

with the signal processing unit and based on a signal of one or more of the readers and/or one or more of the cameras, determining at least once in the time span from the first time point to the second time point a position and/or movement of one or more of the moveable objects relative to the bed;

with the signal processing unit, determining a moveable object movement time course in the time span of the position and/or movement of the one or more of the moveable objects; and using the determined moveable object movement time course in the calculation of the fluid balance.

8. The process according to claim 1, wherein at least one moveable object comprises a container that is configured to hold a drinkable fluid and to be guided to the mouth of the patient, and wherein the process further comprises the steps of:

with the signal processing unit, detecting an event that the container is brought to the mouth of the patient;

with the signal processing unit, measuring how long the patient drinks from the container;

with the signal processing unit, determining an approximate value for an amount of fluid consumed by the patient from the container; and with the signal processing unit, using the approximate value for the calculation of the fluid balance, wherein the signal processing unit uses at least one signal from the reading unit and/or at least one signal from the camera unit and the objects list for the detection and for the determination.

9. The process according to claim 1, wherein a patient's body object, used to care for the patient, is configured to be arranged on a body of the patient or under the body of the patient at least when the patient is lying in bed and is configured to absorb fluid excreted by the patient, and wherein the process further comprises the steps of:

with the signal processing unit determining the weight of the bed at an earlier time point and the weight of the bed at a later time point, wherein both the earlier time point and the later time point lie within the reference time period, wherein either the patient is in the bed at both the earlier time point and the later time point or outside the bed at both the earlier time point and the later time point, and wherein the weights are determined using a signal from the bed scale; and with the signal processing unit, calculating a difference between the weight of the bed at the earlier time point and the weight of the bed at the later time point; and with the signal processing unit, using the difference between the weight of the bed at the earlier time point and the weight of the bed at the later time point to calculate the fluid balance.

10. The process according to claim 9, further comprising the step of, with the signal processing unit and based on at least one signal from the reading unit and/or at least one signal from the camera unit, detecting an event that the patient's body object on or under the patient's body is replaced, wherein the earlier time point is a time point preceding the replacement of the object and the later time point is a time point subsequent of the replacement.

11. The process according to claim 9, wherein the patient's body object used is configured to remain in the bed even when the patient is not in the bed, wherein the signal processing unit uses a time point at which the patient is not in the bed as the earlier time point and uses another time point at which the patient is also not in the bed as the later time point.

12. A system for automated fluid balancing for a patient, wherein the system is configured to be used in a situation in which for a care of the patient a bed is used and at least one moveable object is used or is usable, wherein a machine-readable object marking, configured to distinguish the at least one moveable object from another moveable object, is provided with the or at least one moveable object, and wherein a reference time period is predefined for the fluid balance, the system comprising:

a bed scale that is configured to measure a current weight of the bed at least twice in the reference time period;

a reading unit comprising at least one reader, wherein the reader or each reader has a respective reading area, and the bed is located in the reading area at least during the reference time period and wherein the reading unit is configured to read the marking;

a camera unit comprising at least one camera, wherein the camera or each camera has a respective field of view, and the bed is located in the field of view at least during the reference time period and wherein the camera unit is configured to generate at least one image;

an objects list provided in a computer-evaluable form, wherein the objects list comprises, for each moveable object, marking information for the marking for the moveable object and information about a weight of the moveable object and/or information about an amount of fluid that the moveable object is capable of taking up; and a signal processing unit that is configured to detect a first time point and a second time point, wherein both the first time point and the second time point are within the reference time period, wherein both the first time point and the second time point are positioned such that the bed scale has measured the current weight of the bed at both the first time point and the second time point, and the patient has been in the bed at both the first time point and the second time point, wherein the signal processing unit is configured to derive a weight difference using a signal from the bed scale, wherein the weight difference is a difference between the weight of the patient at the second time point and a weight of the patient at the first time point, wherein the signal processing unit is configured to detect any object that comes into a vicinity of the patient and/or is removed from the vicinity of the patient in the reference time period, the signal processing unit being configured to perform the detection using at least one signal of the reading unit and/or using at least one signal of the camera unit, wherein the signal processing unit is configured to calculate a fluid balance for the patient based on at least one of a derived weight or each derived weight difference of the bed, information on which moveable objects have come into a vicinity of the bed, information on which moveable objects have been removed from the vicinity of the bed, and information on moveable object weight and/or moveable object quantity of fluid included in the objects list for detected moveable objects.

13. The system according to claim 12, wherein the system is configured to measure, with the bed scale, a current weight of the bed at a third time point, the third time point being between the first time point and the second time point;

wherein the signal processing unit is configured to check whether the patient is outside the bed at the third time point, wherein the signal processing unit is configured, in the case that the patient is outside the bed at the third time point, to use the first time point as an exit time point and the subsequent second time point as a return time point, to determine the difference between the weight of the bed at the return time point and the weight of the bed at the exit time point as a difference between the total amount of fluid which is supplied to the patient outside of the bed and the total amount of fluid which leaves the patient outside of the bed in a time span between the exit time point and the return time point, and to use this determined weight difference for calculating the fluid balance.

14. The system according to claim 12, wherein the bed scale is configured to measure a current weight of the bed at least once in a time span from the first time point to the second time point; and the signal processing unit is configured to determine a time course in the time span of the weight of the bed and to use the time course in the calculation of the fluid balance.

15. The system according to claim 12, further comprising a volume flow sensor that is configured to measure a volume flow or mass flow of a fluid through a fluid guide unit into the body of the patient and/or out of the body of the patient, wherein the fluid guide unit is configured to be connected with the patient at least in the time span from the first time point to the second time point;

wherein the signal processing unit is configured to use the measured volume flow or mass flow to calculate the fluid balance and wherein the system is configured to measure the volume flow or mass flow at least in the time span from the first time point to the second time point.

16. The system according to claim 12, further comprising a urine bag scale that is configured to weigh a urine bag in the time span from the first time point to the second time point, wherein the urine bag is configured to be at least temporarily connected to the body of the patient during the time span reaching from the first time point to the second time point, wherein the signal processing unit is configured to determine a time course of the measured weight of the urine bag during the time span from the first time point to the second time point;

wherein the signal processing unit is configured to use the determined urine bag weight time course in the calculation of the fluid balance.

17. The system according to claim 12, further comprising a table scale that is configured to weigh a table in the time span reaching from the first time point to the second time point, wherein moveable objects are placed or can be placed on the table, which moveable objects are used or can be used for the care of the patient, wherein the signal processing unit is configured to determine a time course of the measured weight of the table during the time span from the first time point to the second time point; and wherein the signal processing unit is configured to use the determined table weight time course in the calculation of the fluid balance.

18. The system according to claim 12, wherein the reading unit comprises at least two readers and/or the camera unit comprises at least two cameras, wherein the signal processing unit is configured to determine at least once a position and/or movement of one or more of the moveable objects relative to the bed in the time span from the first time point to the second time point, based on a signal of one or more of the readers and/or one or more of the cameras;

wherein the signal processing unit is configured to determine a moveable object movement time course in the time span of the position and/or movement of the one or more of the moveable objects; and wherein the signal processing unit is configured to use the determined moveable object movement time course for the calculation of the fluid balance.

19. The system according to claim 12, wherein at least one moveable object comprises a container that is configured to hold a drinkable fluid and to be guided to the mouth of the patient, and wherein the system is further configured:

with the signal processing unit, to detect an event that the container is brought to the mouth of the patient;

with the signal processing unit, to measure how long the patient drinks from the container;

with the signal processing unit, to determine an approximate value for an amount of fluid consumed by the patient from the container; and with the signal processing unit, to use the approximate value for the calculation of the fluid balance, wherein the signal processing unit is configured to use at least one signal from the reading unit and/or at least one signal from the camera unit and the objects list for the detection and for the determination.

20. The system according to claim 12, wherein a patient's body object, used to care for the patient, is configured to be arranged on a body of the patient or under the body of the patient, at least when the patient is lying in bed, and is configured to absorb fluid excreted by the patient, wherein the signal processing unit is configured to determine the weight of the bed at an earlier time point and the weight of the bed at a later time point, wherein both the earlier time point and the later time point lie within the reference time period, wherein either the patient is in the bed at both the earlier time point and the later time point or outside the bed at both the earlier time point and the later time point, and wherein the weights are determined using a signal from the bed scale;

wherein the signal processing unit is configured to calculate a difference between the weight of the bed at the earlier time point and the weight of the bed at the later time point; and wherein the signal processing unit is configured to use the difference between the weight of the bed at the earlier time point and the weight of the bed at the later time point to calculate the fluid balance.

* * * * *